(12) United States Patent
Cooks et al.

(10) Patent No.: US 10,656,157 B2
(45) Date of Patent: May 19, 2020

(54) RARE EVENT DETECTION USING MASS TAGS

(71) Applicant: Purdue Research Foundation, West Lafayette, IN (US)

(72) Inventors: Robert Graham Cooks, West Lafayette, IN (US); Zheng Ouyang, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/862,517

(22) Filed: Sep. 23, 2015

(65) Prior Publication Data

US 2016/0086781 A1   Mar. 24, 2016

Related U.S. Application Data

(60) Provisional application No. 62/054,610, filed on Sep. 24, 2014.

(51) Int. Cl.
*G01N 33/58* (2006.01)
*H01J 49/00* (2006.01)
(Continued)

(52) U.S. Cl.
CPC ........... *G01N 33/58* (2013.01); *G01N 33/574* (2013.01); *G01N 33/49* (2013.01);
(Continued)

(58) Field of Classification Search
CPC .. G01N 2458/15; G01N 33/58; G01N 33/574; G01N 33/48; G01N 33/49; H01J 40/00; H01J 40/0031; H01J 49/00; H01J 49/0031; Y10T 436/24; Y10T 436/25; Y10T 436/25125; Y10T 436/255

USPC ........ 436/501, 536, 538, 63, 173, 174, 175, 436/178; 435/7.1, 7.2, 7.23, 29, 5, 6.11; 250/282, 283

See application file for complete search history.

(56) References Cited

U.S. PATENT DOCUMENTS 8,304,718 B2   11/2012   Ouyang et al.
8,486,623 B2 *   7/2013   Monforte .................. C12Q 1/37
                                                    435/6.1
(Continued)

FOREIGN PATENT DOCUMENTS

| WO | 2012/100120 | * | 7/2012 |
| WO | 2015/023480 A1 | | 2/2015 |
| WO | 2015/100221 A2 | | 7/2015 |

OTHER PUBLICATIONS

Thiery-Lavenant et al. Journal of American Society of Mass Spectrometry, vol. 24, Feb. 9, 2013, pp. 609-614.*
(Continued)

*Primary Examiner* — Maureen Wallenhorst
(74) *Attorney, Agent, or Firm* — Brown Rudnick LLP; Adam M. Schoen (57) ABSTRACT

The invention generally relates to methods for rare event detection using mass tags. In certain embodiments, the invention provides methods for detecting a target analyte in a sample that involve conducting an assay that specifically associates a mass tag with a target analyte in a sample, generating ions of the mass tag, and analyzing the generated ions of the mass tag, thereby detecting the target analyte from the sample.

20 Claims, 6 Drawing Sheets

(51) Int. Cl.
G01N 33/574 (2006.01)
G01N 33/49 (2006.01)
(52) U.S. Cl.
CPC .......... G01N 2458/15 (2013.01); H01J 49/00 (2013.01); Y10T 436/24 (2015.01)

(56) References Cited

U.S. PATENT DOCUMENTS

| | | | |
|---|---|---|---|
| 8,986,945 B2 | 3/2015 | Lin et al. | |
| 9,165,754 B2 | 10/2015 | Owen et al. | |
| 2007/0099207 A1* | 5/2007 | Fuchs | B01L 3/502753 435/6.16 |
| 2007/0172827 A1* | 7/2007 | Murakami | C12Q 1/6816 435/6.12 |
| 2008/0113875 A1* | 5/2008 | Chaurand | C12Q 1/68 506/9 |
| 2009/0088332 A1* | 4/2009 | Ju | G01N 33/6848 506/9 |
| 2012/0119079 A1* | 5/2012 | Ouyang | H01J 49/0431 250/282 |
| 2013/0109590 A1 | 5/2013 | Clarizia et al. | |
| 2013/0122516 A1* | 5/2013 | Hong | G01N 27/62 435/7.1 |
| 2013/0280819 A1 | 10/2013 | Cooks et al. | |
| 2014/0264004 A1 | 9/2014 | Cooks et al. | |

OTHER PUBLICATIONS

Ball et al., "Peptide nucleic acid probes with charged photocleavable mass markers," Artificial DNA: PNA and XNA, 1 (2010) 27-35.
Huang, et al., "Induced Nanoelectrospray Ionization for Matrix-Tolerant and High-Throughput Mass Spectrometry," Angew. Chem. Int. Ed. 50, 9907-9910 (2011).
Deng et al., "Strategies for coupling solid-phase microextraction with mass spectrometry," Trends in Analytical Chemistry 2014, 55, 55-67.
Girod et al, "Accelerated bimolecular reactions in microdroplets studied by desorption electrospray ionization mass spectrometry," Chem. Sci., 2 (2011) 501-510.
Harada, et al., "Monoclonal Antibody G6K12 specific for membrane-associated differentiation marker of human stratified squamous epithelia and squamous cell carcinoma," J. Oral Pathol. Med., 22(4):145 152, 1993.
Huang, et al. "Synchronized Inductive Desorption Electrospray Ionization Mass Spectrometry," Angew. Chem. Int. Ed. 50, 2503-2506 (2011).
Hendricks, et al., "Autonomous in Situ Analysis and Real-Time Chemical Detection Using a Backpack Miniature Mass Spectrometer: Concept, Instrumentation Development, and Performance," Anal. Chem., 2014, 86 2900-2908.
Higashi, et al, "Simultaneous Determination of 25-Hydroxyvitamin D2 and 25-Hydroxyvitamin D3 in Human Plasma by Liquid Chromatography-Tandem Mass Spectrometry Employing Derivatization with a Cookson-Type Reagent," Biol Pharm Bull 24, (2001) 738-43; Anal Sci 19 (2003) 941-3.
Huang, et al, "Rapid Screening of Anabolic Steroids in Urine by Reactive Desorption Electrospray Ionization," Analytical Chemistry, 2007, 79 (21), 8327-8332.
Gao, et al., "Handheld Rectilinear Ion Trap Mass Spectrometer", Anal. Chem., 78 (2006) 5994-6002.
Ifa, et al., "Desorption electrospray ionization and other ambient ionization methods: current progress and preview," Analyst, 2010, 135, 669-681.
Inai, et al., "Immunohistochemical detection of an enamel protein-related epitope in rat bone at an early stage of osteogenesis ," Histochemistry, 99(5):335 362, May 1993.
Kerian, et al., "Touch Spray Mass Spectrometry for In Situ Analysis of Complex Samples" Analyst, 139 (2014) 2714-2720.
Knox, et al., "A simple automated solid-phase extraction procedure for measurement of 25-hydroxyvitamin D3 and D2 by liquid chromatography-tandem mass spectrometry," Ann Clin Biochem 46. (2009) 226-30.
Leriche, et al., "Cleavable linkers in chemical biology," Bioorg Med Chem. Jan. 15, 2012;20(2):571-82.
Mulder, et al., "Characterization of two human monoclonal antibodies reactive with HLA-B12 and HLA-B60, respectively, raised by in vitro secondary immunization of peripheral blood lymphocytes," Hum. Immunol., 36(3), 186-192, 1993.
Li, et al "High efficiency tandem mass spectrometry analysis using dual linear ion traps," Analyst, 2014, 139, 4779-4784.
Yu, et al., "Ex vivo culture of circulating breast tumor cells for individualized testing of drug susceptibility," Science, Jul. 11, 2014, 345 216-220.
Narayanan, et al., "Molecular Ionization from Carbon Nanotube Paper," Angew. Chem. Int. Ed., 53: 5936-5940, 2014.
Ouyang, et al., "Miniature Mass Spectrometers," Ann. Rev. Anyl. Chem., 2 (2009) 187-214.
Li, et al., "Miniature Ambient Mass Analysis System" Anal. Chem. 2014, 86, 2909-2916.
Sagi, et al, "Self-Immolative Polymers," J. Amer. Chem. Soc. 130:16, 5434-5435, 2008.
Stauber, et al., "Rapid generation of monoclonal antibody-secreting hybridomas against African horse sickness virus by in vitro immunization and the fusion/cloning technique," J. Immunol. Methods 161:157-168, 1993.
Ren, et al, "Direct mass spectrometry analysis of untreated samples of ultralow amounts using extraction nano-electrospray," Anal. Methods, 2013, 5, 6686.
Venkateswaran, et al., "Production of Anti-Fibroblast Growth Factor Receptor Monoclonal Antibodies by In Vitro Immunization," Hybridoma, 11(6) 729 739, 1992.

* cited by examiner

RARE EVENT DETECTION USING MASS TAGS

RELATED APPLICATION

This application claims the benefit of and priority to U.S. provisional patent application No. 62/054,610, filed Sep. 24, 2014, the content of which is incorporated by reference herein in its entirety.

FIELD OF THE INVENTION

The invention generally relates to methods for rare event detection using mass tags.

BACKGROUND

A significant challenge in science is the detection and characterization of circulating tumor cells (CTC's) which are present in people with solid tumors and are thought to be a route to metastasis. See Min Yu, et al. Science, Jul. 11, 2014, 345 216-220. Recovery of viable cells can facilitate genotyping and hence allow characterization of drug susceptibility.

Current techniques use a blood filtration system that holds white blood cells as well as rare cells and allows the rare cells to be recognized through microscopy after immunological reactions involving fluorescent stains. In such a process, the optical microscopy readout system is reliable but difficult to automate.

SUMMARY

The invention provides a mass spectrometry approach for identifying a rare target analyte in a complex sample, such as circulating tumor cells in a blood sample. Aspects of the invention are accomplished using mass tags. The ionized mass tag is analyzed in a mass spectrometer to determine if the target analyte has been captured from the sample. In that manner, systems and methods of the invention provide a mass spectrometry readout for identifying a rare target analyte in a complex sample that can be easily automated.

In certain embodiments, the invention provides methods that involve conducting an assay that specifically associates a mass tag with a target analyte in a sample, generating ions of the mass tag, and analyzing the generated ions of the mass tag, thereby detecting the target analyte from the sample. In certain embodiments, prior to the generating step, the method further involves a wash step. The generating step may involve inductively generating ions of the mass tag. In certain embodiments, the inductive charging configuration is preferable because it allows for timing of ion formation to be synchronized with injection into the mass analyzer. Alternatively, non-inductive approaches can be used to generate the ions. Analyzing may involve directing the ions into a mass spectrometer (miniature or bench-top) or other type of ion analysis device.

Another aspect of the invention provides methods for detecting a target analyte in a sample that involve applying a voltage to a surface (e.g., a porous surface or a non-porous surface) to generate ions of a mass tag that is specifically associated with a target analyte from a sample, and analyzing the generated ions of the mass tag, thereby detecting the target analyte from the sample. In certain embodiments, the voltage is produced by an electrode that is physically discrete from the surface and is positioned to provide an inductive charge to the surface. As previously mentioned, the inductive charging configuration may be preferable because it allows for timing of ion formation to be synchronized with injection into the mass analyzer. As discussed above, analyzing may involve directing the ions into a mass spectrometer.

The sample may be any type of sample, e.g., a biological sample or a non-biological sample. In certain embodiments, the sample is a biological sample, such as a body fluid sample, such as blood. Similarly, the target analyte can be any component of a sample that is to be specifically detected. In certain embodiments, in which the sample is a biological sample, the target analyte may be a circulating tumor cell.

The methods of the invention may further involve quantifying the mass tag, thereby quantifying the target analyte. Quantifying may include introducing an internal standard during the conducting step. An exemplary internal standard is an isotopically labeled form of the mass tag.

DETAILED DESCRIPTION

The invention generally provides an approach based on mass spectrometry (MS) and mass tags for the identification and quantification of rare target analytes, e.g., small numbers of rare cells in whole blood, including multiplexed recognition of different types of rare targets and high throughput capabilities. The steps in recognition of rare targets may involve using capture moieties tagged by chemical reactions with a recognizable and unique small molecule (mass tag). In certain embodiments, whole blood is filtered and a mass tagged antibody is allowed to undergo immunoaffinity reactions with a suspension of rare cells in blood.

A second filtration step then completes pre-concentration of a large volume of biofluid to a 2D thin film of cells. Most of these cells are white blood cells but there are also antibody-bound rare cells. After levitation in a volume of solvent the mass tag may be released using a releasing agent while isotopically labeled mass tag is being added in a known amount and the number of circulating tumor cells (CTC) of a particular type may be measured by isotope dilution mass spectrometry.

Systems and methods of the invention provide an approach that can reliably identify the presence of one or more targets (e.g., cells) of a particular type in a complex sample, such as a blood sample. There is both a quantitative and a qualitative aspect to the systems and methods of the invention. That is, both the type of target analyte and the number of copies in a given sample are to be determined. In certain embodiments, a type of cell is identified by, for example, immunological methods, with recognition being by a mass tag which, in this scheme, is transferred from the cell bound antibody to an activated receptor surface from which ionization can be performed. This approach involves the use of a MS tag which has these properties: (i) high ionization efficiency, presumably through a permanent charge on nitrogen (ii) strong binding to the immunological agent (iii) ready release from the immunological agent, through pH change or reagent addition and (iv) strong adsorption by the affinity capture reagent and (v) facile release from the affinity capture reagent in the ionization step.

Quantitation will use isotopically labeled forms of the mass tag as internal standards. They may be added in a solution of the release agent so that release and internal standard addition are simultaneous. An alternative approach involves incorporating an isotopically labeled version of the same mass tag into a different antibody that binds to a reference cell type of known concentration.

The resulting mass tag and internal standard samples will contain release agent and other compounds. In one embodiment, quantitation by single stage mass spectrometry is used. In another embodiments, MS/MS is used with quantification by multiple reaction monitoring (MRM) using isotope dilution.

Selection of a capture moiety, e.g., antibody, is based on the specificity for particular disease states. In certain embodiments, any chemical modification of the capture moiety by tagging with a mass selective tag is performed after the antibody is selected.

Selection of the MS tag may be based on (i) nature of antibody (ii) best recognition in mass spectrometry (high ionization efficiency, distinctive mass/charge ratio) (iii) ease of conjugation of the MS tag to the antibody and (iv) ease of release from the antibody. An additional consideration is that it is highly desirable that the derivatizing reagent be comprised of multiple individual units that yield multiple MS tags when cleaved from the antibody to provide a number of separate ionized or ionizable molecules to amplify the signal and so increase MS sensitivity.

Instead of direct MS analysis of the released mass tag it may be pre-concentrated by binding to a chemically modified surface together with the corresponding isotopically labeled standard. The advantage of this approach is that the mass tag can be concentrated onto a small surface area and separated from matrix materials. In initial experiments, an existing Hamilton robot may be used to transfer solution containing the released mass tag and internal standard using a pipette to an Eppendorf tube array where an affinity capture agent will allow further pre-concentration. In other aspects, a simpler mechanical transport system may be used and exposure to the affinity capture agent occurs during transfer. The affinity capture reagent may be held on a spray probe from which ionization occurs. High throughput analysis of many samples may be enabled.

Advantages of mass spectrometry detection are that it allows automation of data acquisition as opposed to zooming in to individual features on microscope slides and visualizing them. It also allows different types of compounds to be measured. Because of limits in size and cost that are likely to be involved in the deployment of the rare cell detection systems, it is highly desirable to use miniature mass spectrometers (described for example in Zheng Ouyang and R. Graham Cooks, Ann. Rev. Anyl. Chem., 2 (2009) 187-214, the content of which is incorporated by reference herein its entirety). The simplest instrument that fulfills these requirements is the ion trap mass spectrometer (D. R. Ifa, et al. Analyst, 2010, 135, 669-681 and R. March and J F J Todd, Practical Aspects of ion Trap Mass Spectrometry, vol. 1, CRC press, Boca Raton, 1995, the content of each of which is incorporated by reference herein its entirety). The miniature MS/MS detector may be based on existing experience with miniature mass spectrometers (L. Li et al. Anal. Chem. 2014, 86 2909-2916). The fact that this instrumentation is readily miniaturized (this has been done several times in different versions of miniature MS at Purdue) and that it can be operated easily with atmospheric pressure ion sources are further advantages. Ion trap mass analyzers also allow ready multiplexing (P. I. Hendricks et al. Anal. Chem., 2014, 86 2900-2908; and S. A. Smith et al. vol IV, pp. 170, the content of each of which is incorporated by reference herein its entirety). The normal requirements for a MS analyzer of high sensitivity, high chemical specificity and at least unit resolution are also met by these instruments. Tandem mass spectrometry (MS/MS) is readily and particularly simply achieved using ion trap instrumentation.

An way of minimizing time and avoiding loss of sample is to use a dual linear (or rectilinear) ion trap (Linfan Li, Xiaoyu Zhou, James W. Hager and Zheng Ouyang, Analyst, 2014, in press, Owen et al. (U.S. Pat. No. 9,165,754), and Ouyang et al. (U.S. patent application Ser. No. 61/865,377), one ion trap being used to collect and store arriving ions while the other is used for mass analysis (and for MS/MS experiments).

Figure 4:
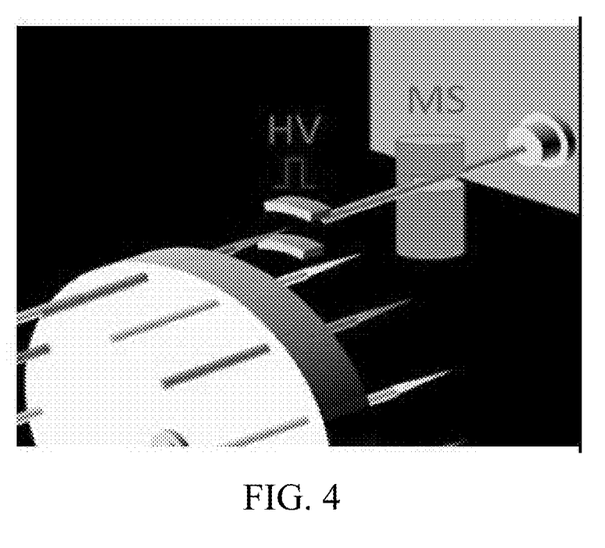
FIG. 4 is an illustration of a high throughput MS measurement using inductive contacts allowing for a blank (wash) and a calibration sample to be run between each six sample probes. This figure shows inductive application of the high voltage (HV) but does not show the transfer of the pipetted solution from the membrane filter to the mass spectrometer (MS).
Figure 5:
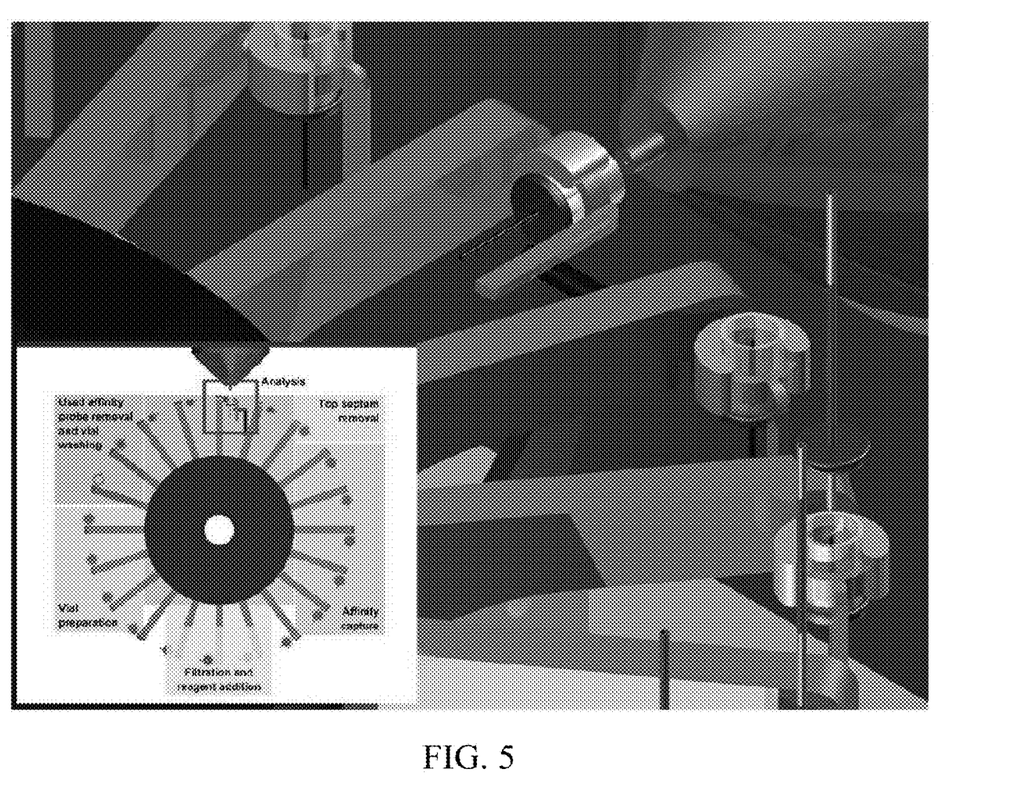
FIG. 5 is an illustration of a sample transfer system showing (inset) the overall system with the filter unit and MS and details of the cartridges which carry the sample in a capillary pipette and the affinity modified needle surface to which analyte molecules are electrophoretically migrated and from which ions are generated using an inductive voltage which causes a spray of ions from the probe. From right to left the cartridges approaching the MS are intact, then the top capillary unit is popped off, then the cartridge is rotated through 90° then the potential is applied for MRM analysis. After analysis a new pipette and spray probe are fitted.
Figure 6:
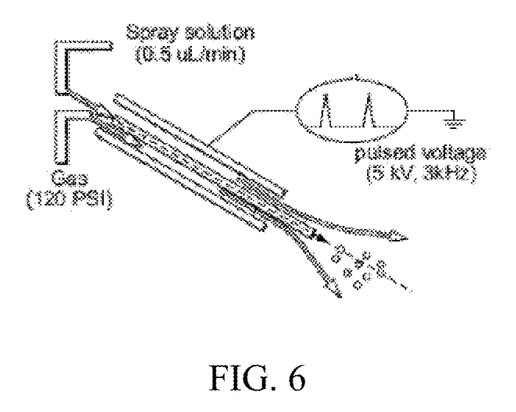
FIGS. 6-9 show exemplary inductive charging system set-ups.
Figure 7:
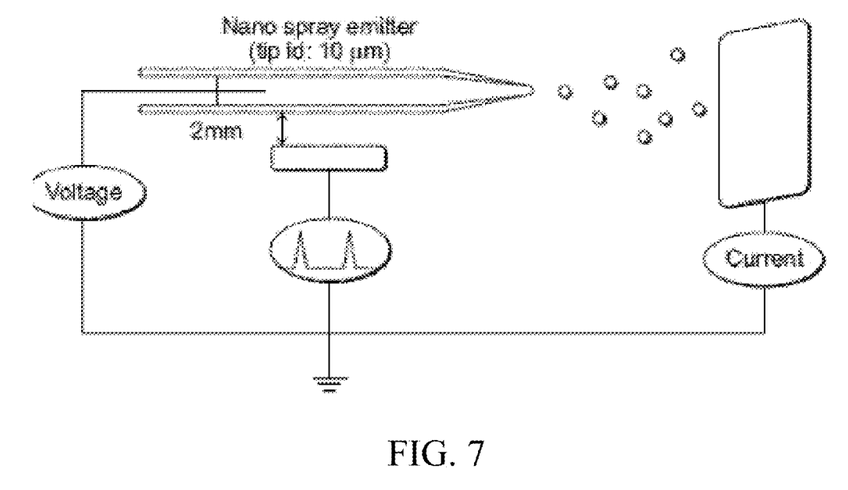
Figure 8:
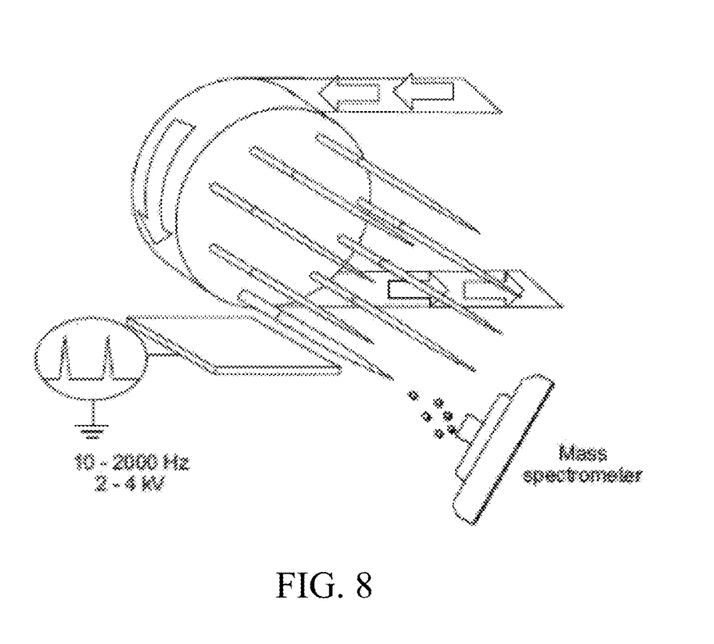
Figure 9:
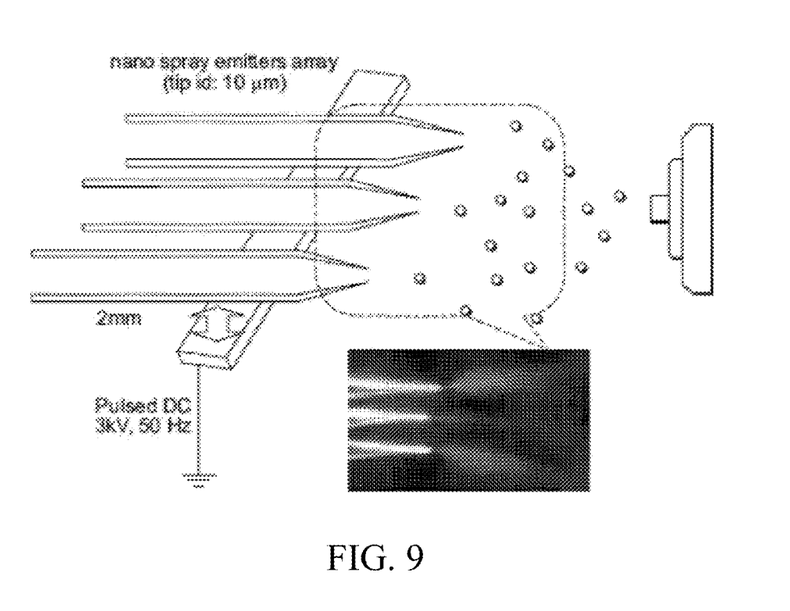

The ultimate aim of the rare target detection methodology is to analyze many hundreds of samples a day at single location. This means that manual presentation of the sample to the mass spectrometer is not possible. FIG. 4 shows a rotating design to implement inductive spray ionization synchronously with ion trap MS operation (G. Huang, et al. Angew. Chem. Int. Ed. 50, 2503-2506 (2011); R. G. Cooks, et al. Angew. Chem. Int. Ed. 50, 9907-9910 (2011)). The method allows multiple samples to be processed efficiently with control of the timing of ionization. FIG. 5 shows another embodiment of a high-throughput system in which pipetted samples are moved from a membrane filter to a mass spectrometer. The system also incorporates inductive ionization. A simple rotating system may be used to transfer the micropipette containing the released MS tag and its isotopically labeled variant from the membrane filter into position at the mass spectrometer. During the transfer a needle bearing the affinity capture reagent may be inserted into the solution to capture the mass tags. Subsequent ionization may be from this needle which may serve as the spray probe on application of an inductive voltage. The rotating design can incorporate a wash step and a cleaning cycle, as well as measurement of a standard solution to facilitate calibration and normalization. The time for transfer may be negligible as it may be used to bind the reagent to the affinity surface and a number of samples may be processed in sequence. The binding step may be improved further by electrophoretic analyte transfer to the surface. Disposable spray probes may be considered.

In certain embodiments, systems and methods of the invention can capture and analyze multiple different mass tags. Given that a number of possible rare cell types might be present, any given sample of blood might be examined for multiple CDC's. The determination will involve measuring MS tag/labeled tag pairs with each measurement taking about 1 to about 2 seconds. To measure multiple cell types specific immunoaffinity agents may be tested for and coordination of different mass tags to these agents may be needed. Isotopically labeled versions of each type of mass tag may be required. For more on the choice of the mass tags see Mass Tags below.

Shown are two exemplary choices for incorporation of internal standards. In the preferred method, the isotopically labeled internal standard is added to the solution as the mass tag is released from the antibody. In the other method, the labeled form of the mass tag is bound to an antibody which complexes with a reference cell of known concentration. The two mass tags are later released and isotope dilution is used to measure their relative amounts.

In an exemplary embodiment, the methodology herein is adapted for the analysis of about 20 to about 200 μL of serum or urine for Vitamin D2 and D3. High efficiency extraction and derivatization may be used to enhance the sensitivity for a direct quantitation with simple procedure. The following experiments may be done to identify the limits in the performance and to develop the solutions for achieving LOQ of 30 ng/mL using only simple procedures.

Solid phase extraction with derivatization and extractive spray. A solid phase probe coated with $C_8$ material (Knox et al, Ann Clin Biochem 46. (2009) 226-30) may be used to collect the vitamin D from serum or urine. The probe may then be inserted in a nanoESI tube containing a solvent with derivatization agent. The Diels-Alder reaction using 4-[2-(6,7-dimethoxy-4-methyl-3-oxo-3,4-dihydroquinoxalyl)ethyl]-1,2,4-triazoline-3,5-dione (DMEQTAD) or 4-(4-nitrophenyl)-1,2,4-triazoline-3,5-dione (NPTAD) has been shown to be effective by improving the ionization efficiency (Higashi et al, Biol Pharm Bull 24, (2001) 738-43; Anal Sci 19 (2003) 941-3). The ethyl acetate may be used initially as the solvent for the extraction, derivatization and nanoESI.

Solid phase extraction with reactive DESI. The derivatization with the reagent in solution in nanoESI might take about 10 to about 60 min. However, previously, it was demonstrated that reactions in charged droplets can be 1000 times faster than the same reactions occurring in bulk solvents (M. Girod et al, Chem. Sci., 2 (2011) 501-510). Solvent containing the derivatization agent may be sprayed directly toward the solid phase extraction probe; the charged droplet containing DMEQTAD, NPTAD or other reagent molecules can pick up the vitamin D and may facilitate a fast, real time derivatization. The reaction products are then analyzed by MS. This approach has been previously applied for direct analysis of steroids in urine (Huang et al, Analytical Chemistry, 2007, 79 (21), 8327-8332).

Mass labels may be conjugated to the antibodies to achieve about 1 to about 3000 cells/10 mL sensitivity and quantitative accuracy. The mass label may be capable of being conjugated to and released from the antibody in straightforward chemical steps. An isotopic form of the MS label may also be acquired or synthesized. In other aspects of the work a new method of label incorporation synthesis based on isotopic exchange in microdroplets may be attempted.

Ideal, high performance mass tags and their isotopically labeled (IL) analogs must meet a number of criteria which include the following: 1. speed and ease of binding and release; 2. functional groups that optimize MS efficiency; 3. easy routes to IL forms; and 4. fragmentation by a few simple, high efficiency pathways.

In other aspects, commercially available small cysteine terminated peptides (e.g. YGMTSR*YFC, where the arginine is fully labeled with 13C6 and 14N4) may be selected. The mass tags may be bound to the antibodies using the N-hydroxysuccinimide protected disulfide, SPDP, and released using dithiothreitol (DTT) or a related reagent TCEP, i.e. mercaptan/disulfide redox chemistry may be used for both capture and release. This nonapeptide (mol. mass 1126.46) has an isotope distribution in which the main carbon isotope represents only 50% of the total molecular ion signal.

It may be desirable in certain aspects to synthesize high performance mass tags. These may include quaternary ammonium cations and/or polyenes for high ionization efficiency (the latter by $Ag^+$ cationization). Binding and release may involve thiol/disulfide chemistry which is well-established in biological chemistry but alternatives like complementary bonding of PNAs (R. J. Ball et al. Artificial DNA: PNA and XNA, 1 (2010) 27-35) could also be worth implementing. Unusual atoms (e.g. multiple fluorines) may be incorporated to place the m/z of the ion in an unusual region (to minimize interference and signal suppression) in the MS. A key consideration may be the nature of the fragmentation; ideally two major competitive channels will dominate with the ratio of the signals verifying the absence of interference (qualifying the MRM transition as suitable for quantitation) and the individual fragment ion intensities representing the amount of material. Absolute signals cannot be used hence the need for the IL analog as internal standard and the measurement of a ratio of corresponding signals in the two MRM transitions.

A factor for high quality work at the very low sample sizes involved is that the internal standards may be specifically labeled. There should little to no distribution either in the degree or the position of the labels. A distribution in the number of labels spreads the precursor ion intensity of several m/z values and reduces signal strength. A distribution in the site of the labels spreads the product ion intensity over m/z values with a non-ideal effect on signal. In addition to these factors, the IL mass tag may be chemically highly pure as it is being introduced directly into the solution which may be analyzed (the clean proposed affinity capture will counter this effect to some degree).

A "composite" mass tag which can be depolymerized to generate a number of individual molecules that are measured by MS may multiply the signal by the number of individual molecules generated. The reverse of isoprene polymerization, for example, may give a set of identical molecules that could be ionized and detected. This consideration may be difficult to combine with all the other factors given above but there is now progress being made on 'self-immolative polymers' which do just this when a trigger group is activated (A. Sagi, et al J. Amer. Chem. Soc. 130 (2008) 5434-5435).

In certain embodiments, antibodies and immunochemistry may be selected based on the particular disease of interest. Three specific antibodies already used with microscopy/fluorescence detection may be chosen for this work.

They are WBC-anti CD45, Cancer cell anti CK8/18 and Cancer cell anti CK19. They may be monoclonal antibodies and their specificity will determine the success of the identification aspect of the assay. It may be necessary to demonstrate that the MS tagged antibodies still bind normally to the rare cells (perhaps in the course of a validation of the other all method using the current microscopy methods). It may also be important to demonstrate that the IL mass tags (the internal standard added to the membrane filter in TCEP) equilibrates with the released unlabeled mass tags during the incubation process and that there is no preferential loss of either in this stage of the work (c.f. the heterogeneous nature of system including the polymer film and whole cells as well as cell debris). Chemical tests may suffice on this point. The same three antibodies may be used in proof-of-principle multiplexing experiments.

Further details and aspects of the invention are described below.

Sample

Methods of the invention involve conducting an assay that specifically associates a mass tag with a target analyte in a sample. The sample may be any type of sample, such as an environmental sample, an agricultural sample, or a biological sample. An exemplary biological sample may be a tissue or body fluid. The sample may be collected in any clinically acceptable manner. A tissue is a mass of connected cells and/or extracellular matrix material, e.g. skin tissue, nasal passage tissue, CNS tissue, neural tissue, eye tissue, liver tissue, kidney tissue, placental tissue, mammary gland tissue, placental tissue, gastrointestinal tissue, musculoskeletal tissue, genitourinary tissue, bone marrow, and the like, derived from, for example, a human or other mammal and includes the connecting material and the liquid material in association with the cells and/or tissues. A body fluid is a liquid material derived from, for example, a human or other mammal. Such body fluids include, but are not limited to, mucous, blood, plasma, serum, serum derivatives, bile, blood, maternal blood, phlegm, saliva, sweat, amniotic fluid, mammary fluid, urine, and cerebrospinal fluid (CSF), such as lumbar or ventricular CSF. A sample may also be a fine needle aspirate or biopsied tissue. A sample also may be media containing cells or biological material. In certain embodiments, the sample is drawn blood or saliva.

Target Analyte

The target analyte is the analyte within the sample to be captured. In the context of biological samples, the target analyte can be any molecule within the sample, such as any molecule within a blood sample. Exemplary target analytes in a biological sample may be a cell (such as a circulating cancer cell, a fetal cell, or a stem cell), a pathogen (such as a bacteria, virus, or a fungus, which are described for example in Clarizia et al., U.S. patent application publication number 2013/0109590, the content of which is incorporated by reference herein in its entirety), or a molecule not within or bound to a cell, such as a nucleic acid or a protein. The target analyte can be a synthetic or non-naturally occurring molecule introduced to a sample, such as a drug. The nucleic acid or protein can be cell free circulating nucleic acids or proteins or those from within a cell based on lysis of the cell. Any standard cell lysis protocol can be used to extract nucleic acid or protein from within a cell within the sample, which protocols are well known in the art. The cancer cell can be for any type of cancer cell and in particular embodiments, it is a circulating tumor cell. Such cells are typically present in people with solid tumors and are thought to be a route to metastasis. See Min Yu, et al. Science, Jul. 11, 2014, 345 216-220, the content of which is incorporated by reference herein in its entirety.

In certain embodiments, the target analyte is considered a rare target analyte within the sample. A rare target analyte (e.g., rare cell) is in contract to a component of the sample that is found in abundance within the sample. A rare target analyte is one in which the target analyte occur with much lower frequency than non-target components of the sample. A rare target analyte is described for example in Lin et al., (U.S. Pat. No. 8,986,945), the content of which is incorporated by reference herein in its entirety. Generally, a rare cell is a cell that is either 1) of a cell type that is less than 1% of the total nucleated cell population in a fluid sample, or 2) of a cell type that is present at less than one million cells per milliliter of fluid sample. In certain embodiments, white blood cells are considered abundant components within the sample and are not considered rare target analytes.

In agricultural or environmental samples, the target analyte may be a pesticide, pathogen, or other molecule to be detected Mass Tag A mass tag refers to a molecule of known mass with high ionization efficiency. The mass tag is the molecule that becomes associated with the target analyte and is subsequently ionized. The detection of the ionized mass tag determines the presence of the target analyte from within the sample. Absence of the mass tag means that the target analyte was not present in the sample. Accordingly, the strategy based on the indirect detection of the target analyte via the mass tag.

An exemplary molecule is one that has high ionization efficiency through a permanent charge on nitrogen. The mass of the tag is chosen so that it is unique to the sample and does not have a mass of any other molecule present in the sample. In other aspects, commercially available small cysteine terminated peptides (e.g. YGMTSR*YFC, where the arginine is fully labeled with 13C6 and 14N4) may be selected.

It may be desirable in certain aspects to synthesize high performance mass tags. These may include quaternary ammonium cations and/or polyenes for high ionization efficiency (the latter by $Ag^+$ cationization). Binding and release may involve thiol/disulfide chemistry which is well-established in biological chemistry but alternatives like complementary bonding of PNAs (R. J. Ball et al. Artificial DNA: PNA and XNA, 1 (2010) 27-35) could also be worth implementing. Unusual atoms (e.g. multiple fluorines) may be incorporated to place the m/z of the ion in an unusual region (to minimize interference and signal suppression) in the MS. A key consideration may be the nature of the fragmentation; ideally two major competitive channels will dominate with the ratio of the signals verifying the absence of interference (qualifying the MRM transition as suitable for quantitation) and the individual fragment ion intensities representing the amount of material. Absolute signals cannot be used hence the need for the IL analog as internal standard and the measurement of a ratio of corresponding signals in the two MRM transitions.

In certain embodiments, a composite mass tag is used. A "composite" mass tag is a tag that can be depolymerized to generate a number of individual molecules that are measured by MS, and may multiply the signal by the number of individual molecules generated. The reverse of isoprene polymerization, for example, may give a set of identical molecules that could be ionized and detected. This consideration may be difficult to combine with all the other factors given above but there is now progress being made on 'self-immolative polymers' which do just this when a trigger group is activated (A. Sagi, et al J. Amer. Chem. Soc. 130 (2008) 5434-5435).

Assays

The methods of the invention involve conducting an assay that specifically associates the mass tag with the target analyte. An exemplary assay uses a capture moiety that specifically binds the target analyte in the sample. The mass tag is associated with, bound to, the capture moiety. Upon specific binding of the capture moiety to the target analyte, the mass tag becomes associated with the target analyte. A separation step is then performed, such as washing away unbound capture moiety or performing a purification that separates the target analyte/capture moiety/mass tag complex from the sample. After the separation step (washing or purification) The mass tag is then eluted from the capture moiety and analyzed. Specifically, an environment can be created that promotes dissociation of the mass tag from the moiety. For example, a pH change can be used to promote dissociation. Alternatively chemical reagents can be used to promote dissociation. Alternatively, heat can be used to promote dissociation. In certain embodiments, a combination of techniques is used, e.g., a combination of pH change and a releasing agent. Binding and release may involve thiol/disulfide chemistry which is well-established in biological chemistry but alternatives like complementary bonding of PNAs (R. J. Ball et al. Artificial DNA: PNA and XNA, 1 (2010) 27-35) can be used.

Specific binding or specific association refers to a binding reaction that is determinative of the target analyte of interest in a heterogeneous population of molecules. Thus, under designated conditions (e.g. immunoassay conditions), the specified capture moiety (e.g., antibody variable domain) binds to its particular "target" and does not bind in a significant amount to other molecules present in a sample. The specific binding/association means that binding is selective in terms of target identity, high, medium or low binding affinity or avidity, as selected. Selective binding is usually achieved if the binding constant or binding dynamics is at least 10 fold different.

The capture moiety may be any molecule known in the art and will depend on the target to be captured and isolated. Exemplary capture moieties include nucleic acids (including nucleic acid probes), proteins, ligands, lectins, antibodies, aptamers, bactertiophages, host innate immunity biomarkers (e.g., CD14), host defense peptides (e.g., defensins), bacteriocins (e.g., pyocins), and receptors.

In particular embodiments, the capture moiety is an antibody. General methodologies for antibody production, including criteria to be considered when choosing an animal for the production of antisera, are described in Harlow et al. (Antibodies, Cold Spring Harbor Laboratory, pp. 93-117, 1988). For example, an animal of suitable size such as goats, dogs, sheep, mice, or camels are immunized by administration of an amount of immunogen, such the target bacteria, effective to produce an immune response. An exemplary protocol is as follows. The animal is injected with 100 milligrams of antigen resuspended in adjuvant, for example Freund's complete adjuvant, dependent on the size of the animal, followed three weeks later with a subcutaneous injection of 100 micrograms to 100 milligrams of immunogen with adjuvant dependent on the size of the animal, for example Freund's incomplete adjuvant. Additional subcutaneous or intraperitoneal injections every two weeks with adjuvant, for example Freund's incomplete adjuvant, are administered until a suitable titer of antibody in the animal's blood is achieved. Exemplary titers include a titer of at least about 1:5000 or a titer of 1:100,000 or more, i.e., the dilution having a detectable activity. The antibodies are purified, for example, by affinity purification on columns containing protein G resin or target-specific affinity resin.

The technique of in vitro immunization of human lymphocytes is used to generate monoclonal antibodies. Techniques for in vitro immunization of human lymphocytes are well known to those skilled in the art. See, e.g., Inai, et al., Histochemistry, 99(5):335 362, May 1993; Mulder, et al., Hum. Immunol., 36(3):186 192, 1993; Harada, et al., J. Oral Pathol. Med., 22(4):145 152, 1993; Stauber, et al., J. Immunol. Methods, 161(2):157 168, 1993; and Venkateswaran, et al., Hybridoma, 11(6) 729 739, 1992. These techniques can be used to produce antigen-reactive monoclonal antibodies, including antigen-specific IgG, and IgM monoclonal antibodies.

Target cells may be recognized and labeled by their affinity for antibodies directed at one or more of the following: ACPP, AFP, albumin, ALCAM, AMAS, ARF6, ARMCX3, ATP1A1, BAG1, BJ-TSA-9, blc-2.beta.HCG, CA125, CA15-3, CA19-9, Cathepsin B1, CD44, CD44v6, CD56, CD66a, CD66b, CD66c, CD66d, CD66e, CD66f, CD147, CDH2, CDK4I, CDKN2A, CDX2, CEA, CLDN3, CLDN4, CLDN5, c-met, CST3, Cytokeratins, CK18, CK19, CK20, Desmoplakin-3, EAG1, EGFR, EGP2, EMA, ErbB2, ESR1, FAK, FOXA2, GalNac-T, GCTFTI5, GFAP, Haptoglobin-.alpha., HCA, hCASK, HE4, HEPA1, hERG, HIP-1, HMB45, HSPA2, IGFR, IVL, KCNK-9, KHDRBS3, Ki67, Kv1.3, LAMB2, Lewis-Y antigen, LIMA, LM06, LUNX, MAGE-3, MAGE-A3, mammoglobin, Maspin, Melan-A, MITF, MPP5, MPST, MUC-1, MUC5AC, NCAM-1, NSDHL, Oct4, OTC, p53, p97, p1B, PCNA, PGR, PMSA, PS-2, PSA, RPS6KA5, S100, S100A1, S100A2, S100B, SLC2A1, Smoothelin, SP-1, SPARC, Surfactant, Telomerase, TFAP2A, TITF1 (TTF1), TFF2, TRAIL, TRIM28, TRPM-8, TYR, Tyrosinase, TYRP1, Ubiquitin thiolesterase, VEGF, WT1, X-protein, ZNF165. In the embodiments where two or more specific binding members are used to label the target cells, each binding member might carry none, the same, or different labels. The apoptotic cancer cells are often further identified by detection of one or more of the following: Phosphatidylserine, DNA fragmentation, Cytochrome C, Caspase. The ratio of identified apoptotic cells to the overall specific rare cell population identified by methods of the current invention may be used as a diagnostic index.

Leriche et al. (Bioorg Med Chem. 2012 Jan. 15; 20(2): 571-82, the content of which is incorporated by reference herein in its entirety), describes methods for generating cleavable linkers, and techniques for coupling a molecule to a capture moiety, such as an antibody, via a cleavable linker.

Ion Generation of the Mass Tag

Any approach for generating ions known in the art may be employed. Ion generation can be accomplished by placing the sample on a porous material and generating ions of the mass tag from the porous material or other type of surface, such as shown in Ouyang et al., U.S. patent application publication number 2012/0119079, the content of which is incorporated by reference herein in its entirety. Alternatively, the assay can be conducted and ions generated from a non-porous material, see for example, Cooks et al., U.S. patent application Ser. No. 14/209,304, now abandoned, the content of which is incorporated by reference herein in its entirety). In certain embodiments, a solid needle probe or surface to which a high voltage may be applied is used for generating ions of the mass tag (see for example, Cooks et al., U.S. patent application publication number 20140264004, the content of which is incorporated by reference herein in its entirety).

In certain embodiments, inductive charging for ion generation is preferable because it allows for timing of ion formation to be synchronized with injection into a mass analyzer. Inductive charging is described for example in Cooks et al. (U.S. patent application publication number 2013/0280819), the content of which is incorporated by reference herein in its entirety. Typically, an inductive charging approach involves a probe or surface and a high voltage source, in which the probe or surface is configured such that the high voltage source is not in contact with spray emitted by the spray emitter and the ions are generated by inductive charging. In such an approach, sample ions are formed by pulsing voltage from a source that is not in contact with the sample to inductively interact with the sample, thereby producing sample ions.

FIGS. 6-9 show exemplary inductive charging system set-ups, including a probe or surface and a high voltage source, in which the probe or surface is configured such that the high voltage source is not in contact with sample. In this manner, the ions are generated by inductive charging, i.e., an inductive method is used to charge the primary microdroplets. This allows droplet creation to be synchronized with injection into a mass analyzer.

In certain embodiments, charged droplet creation is achieved by placing an electrode near a probe or surface (typically 2-5 mm distant) and pulsing it repetitively to high positive potentials (5-7 kV, 50-3,000 Hz, pulse width about 0.2-2 ms). The pulsed positive voltage can be applied to a metal tube (id 250 μm), covering an inner silica capillary which served as the spray emitter tip (id 50 μm) or to another type of surface. Electromagnetic induction produces high electrical fields that result in bursts of charged droplets.

Functionalized Mass Spectrometry Probe

In certain embodiments, aspects of the invention are accomplished using mass tags and a mass spectrometry probe that includes a surface that is functionalized to specifically and releasably bind the mass tags in the sample. The probe specifically captures the mass tag in the sample and that same probe is configured to ionize the sample so that the mass tag is ionized in an environment that causes the mass tag to be dissociated from the binding moiety on the surface of the probe. The ionized mass tag is analyzed in a mass spectrometer to determine if the target analyte has been captured from the sample. In that manner, systems and methods of the invention provide a mass spectrometry readout for identifying a rare target analyte in a complex sample that can be easily automated.

Figure 3:
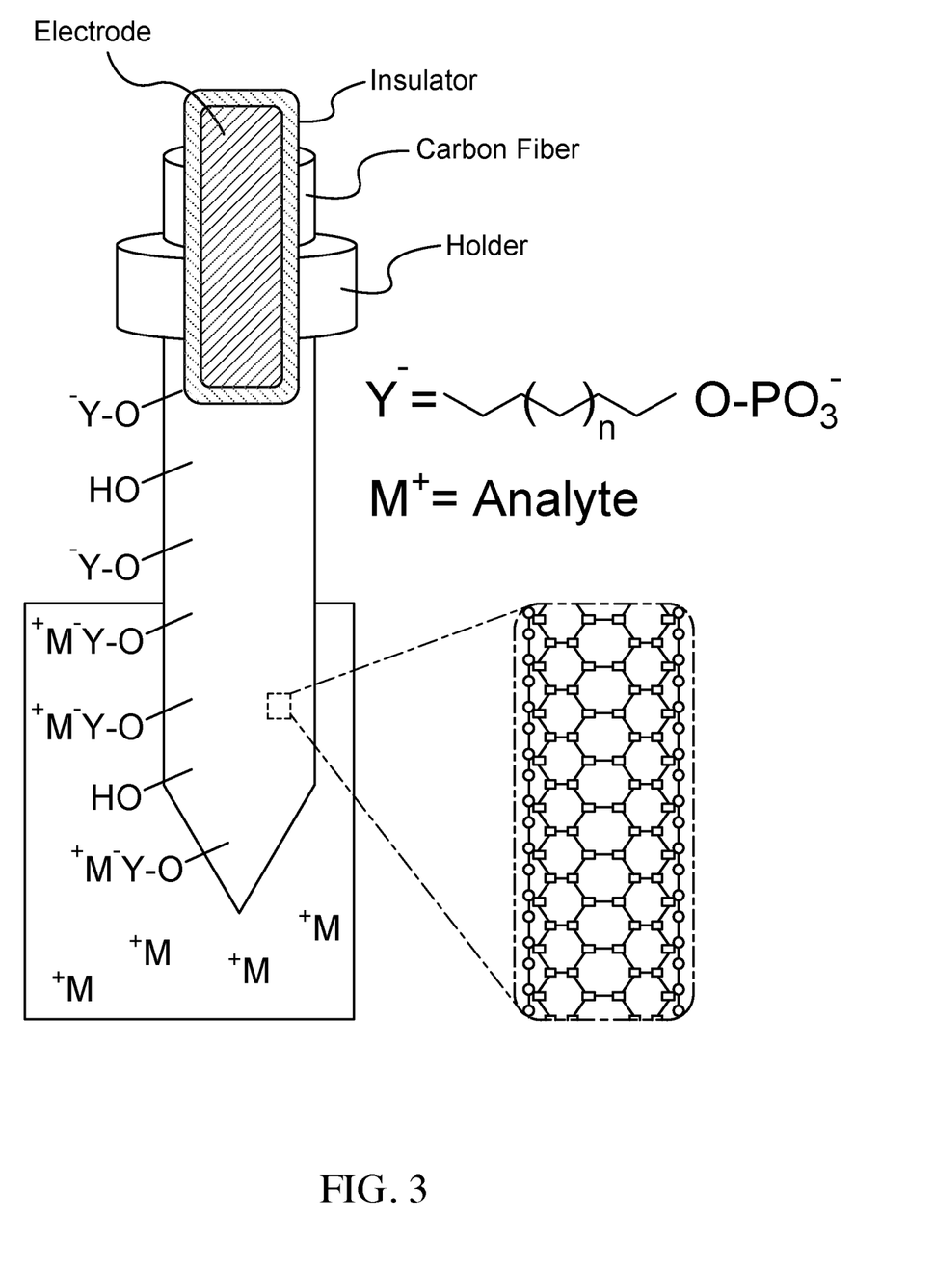
FIG. 3 is an embodiment of a probe of the invention. This version includes a holder region, bound polymeric capture agent, carbon nanotubes for electrical emission and thin solution retention region to hold sample solution during ionization. Modification of the hydroxyl surface to create phosphates is illustrated as an example of chemical derivatization to create an affinity surface.

There are numerous possible configurations for ion generation. One possible configuration is described in Cooks et al., U.S. patent application Ser. No. 14/209,304, now abandoned, the content of which is incorporated by reference herein in its entirety. In certain embodiments, transfer of the released MS tags by binding them to a chemically modified spray probe provides an extra pre-concentration/purification step. Transfer to the affinity surface of the spray probe can either be simply by allowing diffusion in the small volume of sample or it can be done more rapidly by electrophoretic transfer. The spray probes can be disposable units. An embodiment of a spray probe is shown in FIG. 3, which features a cylindrical head unit which can fix the unit in a holder and a conical point which will come to a sharp tip. This design can facilitate spraying of small volumes with spray solvent being applied after affinity capture.

Inductive application of voltage may be invaluable to time ion formation to coincide with MS operations. An electrode may be inserted into the probe, as in a recent design of an inductive ionization source described in Zhang (ASMS Annual Conference, 2014). In a variation, carbon nanotubes may be impregnated into the surface (Narayanan, et al. Angew. Chem. Int. Ed., (2014) 53: 5936-5940 and Cooks et al., U.S. patent application Ser. No. 61/926,713) to give good emission at lower voltages and the covalently bound or polymeric capture agent may be dressed on the surface of the object. Although carbon is one substrate of interest other materials like silicon in the form of needles can be used. An exemplary capture molecule can be a phosphate generated from the carbon surface phenolics in early versions and this basic functionality may be altered as experience of performance dictates. The choice of phosphate is based on the expected strong bonding in the low pH range with quaternary ammonium cationic MS tags. Other variations on the affinity spray probe may be explored, including a version in which the internal surface of a syringe needle is modified.

The affinity capture agent may be located on the surface of the probe. The probe can be of a porous material (see for example, Ouyang et al., U.S. patent application publication number 2012/0119079, the content of which is incorporated by reference herein in its entirety) or a non-porous material (see for example, Cooks et al., U.S. patent application Ser. No. 14/209,304, now abandoned, the content of which is incorporated by reference herein in its entirety). In certain embodiments, the probe is a solid needle probe ("spray probe") to which a high voltage may be applied (see for example, Cooks et al., U.S. patent application Ser. No. 14/209,304, now abandoned, the content of which is incorporated by reference herein in its entirety). The high voltage can be applied inductively (see for example, Cooks et al., U.S. patent application publication number 2013/0280819, the content of which is incorporated by reference herein in its entirety), or non-inductively. In certain embodiment, the voltage may be applied inductively to generate an electrospray. Release of the mass tag from the affinity capture agent (not to be confused with release from the antibody) may be done after washing the surface and using a pH change or specific reagent to effect mass tag release. A minimum volume (some μL) of solvent may be applied during the release/ionization step to maximize sensitivity of ionization. The voltage may be applied inductively to allow chemical reactivity at the affinity surface. Inductive application of the voltage will also allow timing of ion formation to be synchronized with injection into the mass spectrometer (G. Huang, et al. Angew. Chem. Int. Ed. 50, 2503-2506 (2011); R. G. Cooks, et al. Angew. Chem. Int. Ed. 50, 9907-9910 (2011), the content of each of which is incorporated by reference herein in its entirety). MS/MS (MRM) may be used to measure the proportions of labeled and unlabeled capture agent. From the known amount of isotopically labeled recognition agent and the (approximate) number of antibodies bound per cell, isotope dilution can be used to count the number of rare cells.

A unique aspect of the systems and methods of the invention is that the surface of the probe has a double role as the locus of chemical pre-concentration and of ionization. Systems of the invention allow for the volume of solution to be minimized, which maximizes ion currents.

In certain aspects, the invention provides systems for analyzing a sample that include a probe having a surface that includes at least one moiety coupled thereto that specifically and releasably binds a target analyte in a sample. The system additionally includes an electrode operably associated with the probe to impart a voltage to the probe, and a mass analyzer operably associated with the probe to receive ions expelled from the probe. The electrode can be coupled to the probe in any manner, such as a physical coupling to the probe or a configuration in which the electrode is physically discrete from the probe and is positioned to provide an inductive charge to the surface of the probe. In certain embodiments, the inductive charging configuration is preferable because it allows for timing of ion formation to be synchronized with injection into the mass analyzer.

The probe surface may be composed of numerous different types of materials. In certain embodiments, the surface is a porous surface. In other embodiments, the surface is a non-porous surface. In certain embodiments, the probe is a solid needle. In other embodiments, the probe is a needle with a hollow bore there through.

Other aspects of the invention provide methods for analyzing a sample. Those methods may involve contacting a sample including a target analyte to a probe having a surface that includes at least one moiety coupled thereto that specifically and releasably binds the target analyte in the sample, thereby binding the target analyte to the surface of the probe. A voltage is applied to the surface (inductively or non-inductively) in an environment that allows dissociation of the target analyte from the moiety to thereby generate ions of the analyte. The generated ions are then analyzed.

The target analyte can be any molecule to be analyzed. In certain embodiments, the target analyte is a mass tag. In certain embodiments, the sample further includes an isotopically labeled form of the mass tag that has been spiked into the sample as an internal standard. The isotopically labeled form of the mass tag is also bound by the probe and ions of the isotopically labeled form of the mass tag are analyzed along with ions of the mass tag.

An environment can be created that promotes dissociation of the mass tag from the moiety. For example, a pH change can be used to promote dissociation. Alternatively chemical reagents can be used to promote dissociation. Alternatively, heat can be used to promote dissociation. In certain embodiments, a combination of techniques is used, e.g., a combination of pH change and a releasing agent.

Other aspects of the invention provide methods for detecting a target analyte in a biological sample. Those methods may involve introducing a sample to a capture moiety that specifically binds a target analyte in the sample to thereby form a target analyte/capture moiety complex. The capture moiety includes a mass tag. The sample is filtered to capture the target analyte/capture moiety complex. The mass tag is released from the capture moiety of the target analyte/capture moiety complex. The mass tag is contacted to a probe having a surface that includes at least one moiety coupled thereto that specifically and releasably binds the mass tag, thereby binding the mass tag to the surface of the probe. A voltage is applied to the surface in an environment that allows dissociation of the mass tag from the moiety to thereby generate ions of the mass tag. The generated ions of the mass tag are then analyzed, thereby detecting the target analyte from in the biological sample. Analyzing can encompass many different approaches, and an exemplary approach is to direct the ions into a mass spectrometer.

In certain embodiments, prior to the contacting step, the method further includes introducing an isotopically labeled form of the mass tag, which is also bound by the probe and analyzed along with the ions of the mass tag. Any type of capture moiety may be used, and an exemplary capture moiety is an antibody.

The sample may be any type of sample, e.g., a biological sample or a non-biological sample. In certain embodiments, the sample is a biological sample, such as a body fluid sample, such as blood. Similarly, the target analyte can be any component of a sample that is to be specifically detected. In certain embodiments, in which the sample is a biological sample, the target analyte may be a circulating tumor cell.

As already mentioned, any environment can be created that promotes dissociation of the mass tag from the moiety. For example, a pH change can be used to promote dissociation. Alternatively chemical reagents can be used to promote dissociation. Alternatively, heat can be used to promote dissociation. In certain embodiments, a combination of techniques is used, e.g., a combination of pH change and a releasing agent.

Ion Analysis

Figure 1:
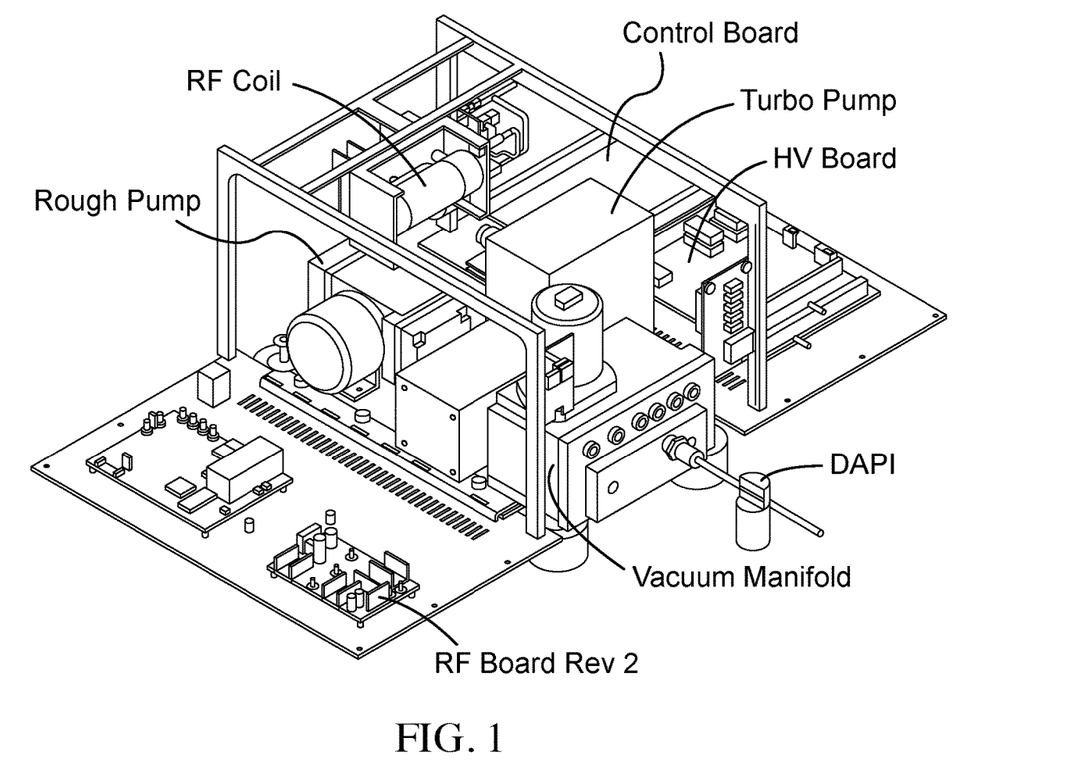
FIG. 1 is an illustration of an exemplary type of miniature mass spectrometer.

In certain embodiments, the ions are analyzed by directing them into a mass spectrometer (bench-top or miniature mass spectrometer). FIG. 1 is a picture illustrating various components and their arrangement in a miniature mass spectrometer. The control system of the Mini 12 (Linfan Li, Tsung-Chi Chen, Yue Ren, Paul I. Hendricks, R. Graham Cooks and Zheng Ouyang "Miniature Ambient Mass Analysis System" Anal. Chem. 2014, 86 2909-2916, DOI: 10.1021/ac403766c; and 860. Paul I. Hendricks, Jon K. Dalgleish, Jacob T. Shelley, Matthew A. Kirleis, Matthew T. McNicholas, Linfan Li, Tsung-Chi Chen, Chien-Hsun Chen, Jason S. Duncan, Frank Boudreau, Robert J. Noll, John P. Denton, Timothy A. Roach, Zheng Ouyang, and R. Graham Cooks "Autonomous in-situ analysis and real-time chemical detection using a backpack miniature mass spectrometer: concept, instrumentation development, and performance" Anal. Chem., 2014, 86 2900-2908 DOI: 10.1021/ac403765x, the content of each of which is incorporated by reference herein in its entirety), and the vacuum system of the Mini 10 (Liang Gao, Qingyu Song, Garth E. Patterson, R. Graham Cooks and Zheng Ouyang, "Handheld Rectilinear Ion Trap Mass Spectrometer", Anal. Chem., 78 (2006) 5994-6002 DOI: 10.1021/ac061144k, the content of which is incorporated by reference herein in its entirety) may be combined to produce the miniature mass spectrometer shown in FIG. 1 It may have a size similar to that of a shoebox (H20×W25 cm×D35 cm). In certain embodiments, the miniature mass spectrometer uses a dual LIT configuration, which is described for example in Owen et al. (U.S. Pat. No. 9,165,754), and Ouyang et al. (U.S. patent application Ser. No. 61/865,377), the content of each of which is incorporated by reference herein in its entirety.

The mass spectrometer (miniature or benchtop), may be equipped with a discontinuous interface. A discontinuous interface is described for example in Ouyang et al. (U.S. Pat. No. 8,304,718) and Cooks et al. (U.S. patent application publication number 2013/0280819), the content of each of which is incorporated by reference herein in its entirety.

Figure 2:
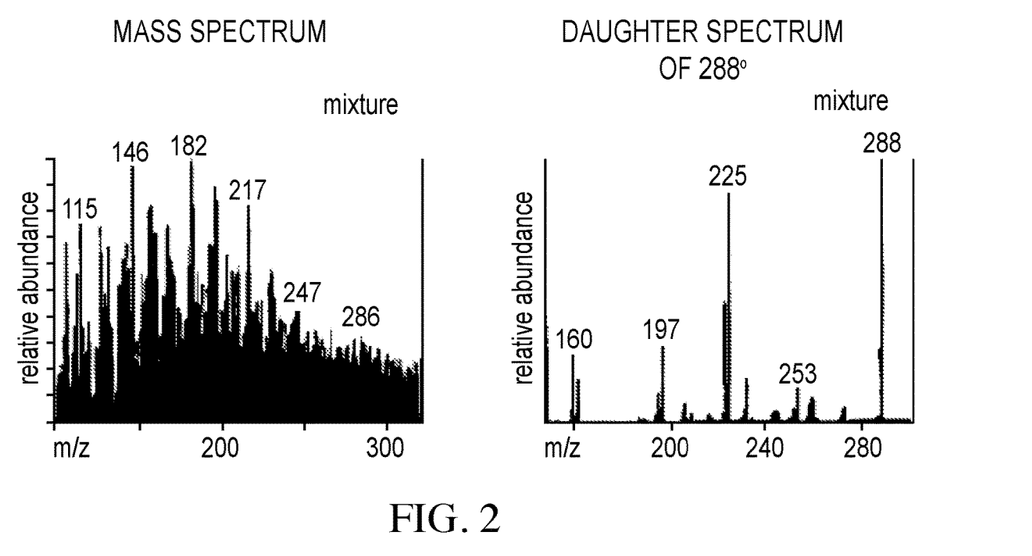
FIG. 2 is an illustration of improved S/N in MS/MS vs. single stage MS in trace analysis.

The factors that should control detection sensitivity are the combined efficiency of all the steps in the chemistry, the number of tags per antibody, the number of antibodies per cell and the number of ions per mass tag, the ionization sensitivity in the MS, the S/N ratio in the MS, the number of different transitions corresponding to different mass tags that are being measured, and the MS acquisition time. However, in ultratrace analysis like this, it is often the magnitude of the chemical noise that determines performance. It is for this reason that in the case of complex mixtures, MS/MS often gives lower detection limits than does the normal MS, even though the total signal in the latter case may be orders of magnitude greater. An illustration of this situation showing the improved signal/noise ratios in MS/MS spectra is shown in FIG. 2.

Methods herein are designed so that the final sample is as 'clean' as possible. Given its small amount, the loss in signal in a MS/MS experiment might be too great. So it is possible that MS might suffice. Note that the chemical noise sources of concern include the release reagent, impurities in the internal standard and in the solvent and transfer containers and trace biochemical and cell degradation products as well as residual chemicals in the instrumentation.

The need for detection sensitivity can be appreciated by considering a few numbers. Assuming 1000 molecules of antibody bind to a single cell, there are $10^3$ molecules in 10 mL i.e. 1 molecule in $10^{18}$ water, i.e. for mol. wt. 400 about 1 attogram and if final vol is 10 µL, the concentration is $10^{-13}$ g/L. This concentration is extraordinarily low and so is the volume and the measurement time may be very limited. There are two conclusions i) it may be desirable to increase the molecular mass of the mass tag, provided the considerations below are satisfied; ii) temporal control of the ionization process and ion injection in the ion trap is important. Such temporal control has been demonstrated using inductive ionization (Cooks et al. U.S. patent application publication number 2013/0280819).

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A method for detecting a target analyte in a sample, the method comprising:
    conducting an assay that specifically associates a mass tag with a target analyte in a sample;
    depolymerizing the mass tag to generate a plurality of molecules that are dissociated from the target analyte;
    capturing the plurality of molecules via an affinity agent on a spray probe, thereby pre-concentrating the plurality of molecules;
    generating, via the spray probe, a plurality of ions from the plurality of molecules; and
    analyzing the plurality of ions, thereby detecting the target analyte from the sample.

2. The method according to claim 1, wherein the generating step comprises inductively generating the plurality of ions from the plurality of molecules.

3. The method according to claim 1, wherein analyzing comprises directing the ions into a mass spectrometer.

4. The method according to claim 1, wherein the sample is a biological sample.

5. The method according to claim 4, wherein the biological sample is a blood sample.

6. The method according to claim 5, wherein the target analyte is a circulating tumor cell.

7. The method according to claim 1, further comprising quantifying the plurality of ions from the plurality of molecules, thereby quantifying the target analyte.

8. The method according to claim 7, wherein quantifying comprises introducing an internal standard to the sample during the conducting step.

9. The method according to claim 8, wherein the internal standard is an isotopically labeled form of the mass tag.

10. The method according to claim 1, wherein prior to the generating step, the method comprising a wash step.

11. A method for detecting a target analyte in a sample, the method comprising:
    applying a voltage to a spray probe to generate a plurality of ions from a plurality of molecules, the plurality of molecules being generated from depolymerization of a mass tag that is specifically associated with a target analyte from a sample wherein the plurality of molecules are dissociated from the target analyte, and are captured via an affinity agent on the spray probe, thereby pre-concentrating the plurality of molecules; and
    analyzing the plurality of ions from the plurality of molecules, thereby detecting the target analyte from the sample.

12. The method according to claim 11, wherein the voltage is produced by an electrode that is physically discrete from the spray probe and is positioned to provide an inductive charge to the spray probe.

13. The method according to claim 11, wherein the spray probe is a porous spray probe.

14. The method according to claim 11, wherein analyzing comprises directing the ions into a mass spectrometer.

15. The method according to claim 11, wherein the sample is a biological sample.

16. The method according to claim 15, wherein the biological sample is a blood sample.

17. The method according to claim 16, wherein the target analyte is a circulating tumor cell.

18. The method according to claim 11, further comprising quantifying the plurality of ions from the plurality of molecules, thereby quantifying the target analyte.

19. The method according to claim 18, wherein quantifying comprises analyzing ions of an internal standard while analyzing the plurality of ions from the plurality of molecules.

20. The method according to claim 19, wherein the internal standard is an isotopically labeled form of the mass tag.

* * * * *